(12) United States Patent
Doddroe et al.

(10) Patent No.: US 8,317,873 B2
(45) Date of Patent: Nov. 27, 2012

(54) POLYMERIC PROSTHETIC LINER WITH CONTROLLED STRETCH CHARACTERISTICS

(75) Inventors: Jeffrey L. Doddroe, Washington Court House, OH (US); Christopher T. Kelley, Grandview Heights, OH (US); Larry Gail Rowe, Jr., Williamsport, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 139 days.

(21) Appl. No.: 12/711,234

(22) Filed: Feb. 23, 2010

(65) Prior Publication Data

US 2011/0208321 A1 Aug. 25, 2011

(51) Int. Cl.
*A61F 2/80* (2006.01)
(52) U.S. Cl. .......................................... 623/36
(58) Field of Classification Search ............... 623/32–37
See application file for complete search history.

(56) References Cited

U.S. PATENT DOCUMENTS

| | | |
|---|---|---|
| 1,319,637 A | 10/1919 | Blevens |
| 1,497,219 A | 6/1924 | Martino |
| 2,002,064 A | 5/1935 | Kohl |
| 2,202,598 A | 5/1940 | Peterson |
| 2,666,208 A | 1/1954 | Funk |
| 2,671,225 A | 3/1954 | Schoene et al. |
| 2,703,405 A | 3/1955 | Smallberg |
| 2,824,559 A | 2/1958 | Sullivan |
| 3,084,685 A | 4/1963 | Lewis |
| 3,132,648 A | 5/1964 | Scholl |
| 3,239,478 A | 3/1966 | Harlan |
| 3,265,765 A | 8/1966 | Holden et al. |
| 3,375,821 A | 4/1968 | Meek |
| 3,417,413 A | 12/1968 | Gage |
| 3,451,232 A | 6/1969 | Belzidsky |
| 3,457,566 A | 7/1969 | Artzt |
| 3,520,002 A | 7/1970 | Wellington |
| 3,548,420 A | 12/1970 | Spence |
| 3,595,942 A | 7/1971 | Wald et al. |

(Continued)

FOREIGN PATENT DOCUMENTS

CA 2190764 11/2007

(Continued)

OTHER PUBLICATIONS

Statement of Relevancy filed in U.S. Appl. No. 09/121,300 with attachments of Silopad™ Silosheath Brochure (3 pp.); Silosheath Invoice (6 pp.) dated Nov. 1, 1993, with photo of item No. 12155 (Silosheath/Medium; corresponding to Item No. 12155 on the Invoice); Silipos Domestic Price List (7 pp.); 2150 Liberty Drive; L.P.O. Box 211; Niagara Falls, NY 14303; Effective May 1994.

(Continued)

*Primary Examiner* — Bruce E Snow
(74) *Attorney, Agent, or Firm* — Standley Law Group LLP

(57) ABSTRACT

A controlled-stretch prosthetic liner comprising a polymeric material covered with at least a stretch-controlling fabric. Certain liner types, such as below knee (BK) liners, may also include a panel of more stretchable fabric so as to prevent any interference with knee flexion. The polymeric material of the liner may also be used to control liner stretch, such as by adding Kevlar pulp or other materials that increase the strength and reduce the elasticity of the polymeric material and/or by reducing the amount of plasticizer(s) present therein. The stretch-controlling fabric, possibly in conjunction with the polymeric material, acts to limit the longitudinal stretch of the liner while not adversely affecting the radial stretch thereof.

27 Claims, 10 Drawing Sheets

U.S. PATENT DOCUMENTS

| | | | |
|---|---|---|---|
| 3,598,127 A | 8/1971 | Wepsic |
| 3,600,717 A | 8/1971 | McKeehan |
| 3,663,973 A | 5/1972 | Spence |
| 3,676,387 A | 7/1972 | Lindlof |
| 3,732,578 A | 5/1973 | Pollack |
| 3,827,999 A | 8/1974 | Crossland |
| 3,855,677 A | 12/1974 | Belzidsky |
| 3,970,081 A | 7/1976 | Applegate |
| 3,971,194 A | 7/1976 | Morgan |
| 3,983,870 A | 10/1976 | Herbert et al. |
| 4,018,646 A | 4/1977 | Ruffo et al. |
| 4,116,236 A | 9/1978 | Albert |
| 4,183,984 A | 1/1980 | Browers et al. |
| 4,201,203 A | 5/1980 | Applegate |
| 4,250,578 A | 2/1981 | Barlow |
| 4,369,284 A | 1/1983 | Chen |
| 4,381,380 A | 4/1983 | LeVeen et al. |
| 4,474,573 A | 10/1984 | Detty |
| 4,502,234 A | 3/1985 | Schaefer et al. |
| 4,517,688 A | 5/1985 | May et al. |
| 4,542,169 A | 9/1985 | Costerton |
| 4,590,123 A | 5/1986 | Hashimoto et al. |
| 4,618,213 A | 10/1986 | Chen |
| 4,635,626 A | 1/1987 | Lerman |
| 4,663,413 A | 5/1987 | Ward et al. |
| 4,671,267 A | 6/1987 | Stout |
| 4,814,375 A | 3/1989 | Esposito |
| 4,822,371 A | 4/1989 | Jolly et al. |
| 4,832,010 A | 5/1989 | Lerman |
| 4,840,635 A | 6/1989 | Smith et al. |
| 4,842,931 A | 6/1989 | Zook |
| 4,853,978 A | 8/1989 | Stockum |
| 4,908,037 A | 3/1990 | Ross |
| 4,923,474 A | 5/1990 | Klasson et al. |
| 4,923,475 A | 5/1990 | Gosthnian et al. |
| 4,990,556 A | 2/1991 | Shimizu et al. |
| 5,007,937 A | 4/1991 | Fishman et al. |
| 5,083,361 A | 1/1992 | Rudy |
| 5,098,421 A | 3/1992 | Zook |
| 5,108,456 A | 4/1992 | Coonan |
| 5,154,690 A | 10/1992 | Shiono |
| 5,201,773 A | 4/1993 | Carideo |
| 5,201,774 A | 4/1993 | Greene |
| 5,211,667 A | 5/1993 | Danforth |
| 5,218,056 A | 6/1993 | Santiyanont et al. |
| 5,221,534 A | 6/1993 | DesLauriers et al. |
| 5,246,464 A | 9/1993 | Sabolich |
| 5,258,036 A | 11/1993 | Edenbaum et al. |
| 5,258,037 A | 11/1993 | Caspers |
| 5,262,468 A | 11/1993 | Chen |
| 5,263,923 A | 11/1993 | Fujimoto |
| 5,263,990 A | 11/1993 | Handal |
| 5,314,496 A | 5/1994 | Harris et al. |
| 5,314,497 A | 5/1994 | Fay et al. |
| 5,334,446 A | 8/1994 | Quantrille et al. |
| 5,334,646 A | 8/1994 | Chen |
| 5,336,708 A | 8/1994 | Chen |
| 5,376,131 A | 12/1994 | Lenze et al. |
| 5,376,132 A | 12/1994 | Caspers |
| 5,387,245 A | 2/1995 | Fay et al. |
| 5,399,627 A | 3/1995 | Diehl et al. |
| 5,405,405 A | 4/1995 | Love |
| 5,411,037 A | 5/1995 | Hess et al. |
| 5,443,525 A | 8/1995 | Laghi |
| 5,464,384 A | 11/1995 | Cromartie |
| 5,464,443 A | 11/1995 | Wilson et al. |
| 5,480,455 A | 1/1996 | Norvell |
| 5,497,789 A | 3/1996 | Zook |
| 5,507,834 A | 4/1996 | Laghi |
| 5,507,836 A | 4/1996 | Pohlig |
| 5,508,334 A | 4/1996 | Chen |
| 5,534,496 A | 7/1996 | Lee et al. |
| 5,538,500 A | 7/1996 | Peterson |
| 5,555,584 A | 9/1996 | Moore et al. |
| 5,571,208 A | 11/1996 | Caspers |
| 5,593,454 A | 1/1997 | Helmy |
| 5,603,122 A | 2/1997 | Kania |
| 5,633,286 A | 5/1997 | Chen |
| 5,656,023 A | 8/1997 | Caprio et al. |
| 5,728,167 A | 3/1998 | Lohmann |
| 5,728,168 A | 3/1998 | Laghi |
| 5,746,772 A | 5/1998 | Jacobs |
| 5,769,809 A | 6/1998 | Witzel |
| 5,792,531 A | 8/1998 | Littleton et al. |
| 5,830,237 A | 11/1998 | Kania |
| 5,854,372 A | 12/1998 | Henze et al. |
| 5,888,216 A | 3/1999 | Haberman |
| 5,994,612 A | 11/1999 | Watkins |
| 6,025,067 A | 2/2000 | Fay |
| 6,059,834 A | 5/2000 | Springs |
| 6,063,125 A | 5/2000 | Arbogast et al. |
| 6,117,176 A | 9/2000 | Chen |
| 6,136,039 A | 10/2000 | Kristinsson et al. |
| 6,231,617 B1 | 5/2001 | Fay |
| 6,406,499 B1 | 6/2002 | Kania |
| 6,440,345 B1 | 8/2002 | Hellberg |
| 6,454,812 B1 | 9/2002 | Laghi |
| 6,485,776 B2 | 11/2002 | Janusson et al. |
| 6,552,109 B1 | 4/2003 | Chen |
| 6,592,539 B1 | 7/2003 | Einarsson et al. |
| 6,761,742 B2 | 7/2004 | Caspers |
| 6,964,688 B1 | 11/2005 | Kania |
| 7,004,919 B2 | 2/2006 | Gaylord et al. |
| 7,291,182 B1 | 11/2007 | Kania |
| 7,344,568 B2 | 3/2008 | Chen |
| 2002/0183859 A1* | 12/2002 | Houser ............................. 623/36 |
| 2004/0137178 A1* | 7/2004 | Janusson et al. ............. 428/35.7 |
| 2005/0240283 A1 | 10/2005 | Kania |
| 2010/0274363 A1* | 10/2010 | Laghi et al. ..................... 623/36 |

FOREIGN PATENT DOCUMENTS

| | | |
|---|---|---|
| DE | 4321182 | 12/1994 |
| EP | 0955964 | 10/2006 |
| EP | 1618858 | 9/2008 |
| EP | 1736122 | 9/2009 |
| FR | 2581859 | 11/1986 |
| GB | 2213380 | 8/1989 |
| GB | 2261358 | 5/1993 |
| JP | 64-32861 | 2/1989 |
| SU | 1739990 | 6/1992 |
| WO | 9323472 | 11/1993 |
| WO | 9424965 | 11/1994 |
| WO | 9505792 | 3/1995 |
| WO | 9527756 | 10/1995 |
| WO | 9629033 | 9/1996 |
| WO | 9804218 | 2/1998 |

OTHER PUBLICATIONS

Silosheath™ Classic Apr. 30, 2001 Webpage Printout (2 pp.).
Silosheath Soft Socket Gel Liner Brochure (2 pp.); Prices good from Mar. 15, 1994 to Jun. 15, 1994; Silipos; 2150 Liberty Drive; L.P.O. Box 211; Niagara Falls, NY 14304; Toll free: 1-800-229-4404.
SiloLiner™ Mar. 8, 1999 Webpage Printout (2 pp.).
5 SiloLiner™ Feb. 1999 Brochure (2 pp.); Silipos; 7049 Williams Road; L.P.O. Box 211; Niagara Falls, NY 14304; Toll free: (800) 229-4404; www.silipos.com.
Silopos Special! Advertisement, Offer Good through Nov. 30, 1994, (1 pp.) Knit-Rite, Incorporated, 2020 Grand Avenue, P.O. Box 410208, Kansas City, MO 64141-0208: (816) 221-5200; Fax: (816) 221-2896.
Technical Bulletin—Shell Chemical Company: KRATON® Thermoplastic Rubbers and in Oil Gels; Jun. 1992; SC: 1102-89; SC: 1393-92.
ICEFLEX™ Endurance Brochure (2 pp.); Distributors in the United States & Canada: (1) Cascade, Tel: 800-888-0865; (2) Knit-Rite, Tel: 800-821-3094; (3) Orto-Ped, Tel: 800-363-8726; (4) PEL, Tel: 800-321-1264; (5) SPS, Tel: 800-767-7776; Össur, www.ossur.com.
IPOS Orthopadie Industriell Brochure, "The advantages of the ipocon® compression sheath," (2pp.).
Alpha Cushion and Locking Liner Brochures (Jan. 14, 1997); (8 pp.) Ohio Willow Wood Company; 15441 Scioto Darby Road; P.O. Box 130; Mt. Sterling, OH; 43143; Tel: 800-848-4930.
ALPS BetaLiner . . . with Gel and Spandex for Extraordinary Comfort & Cushioning (1 pp.); 2895 42nd Ave. N, St. Petersburg, FL 33714; Tel: 1-800-574-5426; (813) 528-8566; Fax: (813) 528-8862; www.oandp.com/alps.

ALPS Gel-Sheath (1 pp.); Faxed Jul. 24, 1997; ALPS South Corp.; 2895 42nd Ave. N, St. Petersburg, FL 33714; Tel: (813) 528-8566; 1-800-574-5426; Fax: (813) 528-8862; www.oandp.com/alps.
Introducing ALPS GelSock . . . with a Gel Interlayer for Extraordinary Comfort & Cushioning (1 pp.); ALPS South Corp., 2895 42nd Ave. N, St. Petersburg, FL 33714; Tel: (813) 528-8566; 1-800-574-5426; Fax: (813) 528-8862; www.oandp.com/alps.
TEC Interface Systems Accident (12 pp.), Tec Interface Systems.
Total Environment Control . . . Again and Again! (4 pp.), Tec Interface Systems, 510 North 25th Avenue, St. Cloud, MN 56303-3255.
New Products from Össur, Iceross, Comfort™, "The Ultimate in silicone gel suspension from Össur, the silicone specialist," (1 pp.), Nov. 1997, Distributed by: SPS Orthotic Prosthetic Supplies (800-767-7776).
Otto Bock Gel-Strumpf, Derma Seal, Advertisement, Unknown Place of Publication, Unknown date (English Translation).
Pel Supply Co., Prosthetic Catalog, pp. 166, 170, 171 & 194, 1994.
Welcome to Silipos, 1994 Catalog of Silipos Advanced Polymer Technology, handwritten date 1994.
Haws, J.R. and Wright, R.R, Block Polymers, Handbook of Thermoplastic Elastomers (pp. 72-102)(Van Nostrand Reinhold Company, 1979) New York, NY, USA.
Comfort Zone, Silosheath Product Line, O&P Business News dated Sep. 1, 1994 (Advertisement of Silipos, p. 9).
New Introductory Price! Double Cushion Silosheath, Silosheath Product Line, Silipos Advertisement (O&P Business News handwritten date of Oct. 1, 1994) (Advertisement of Silipos).
Comfort Zone Single Socket Gel Liner, Silosheath Product Line, O&P Business News dated Jan. 1, 1995 (Advertisement of Silipos, p. 16).
Soft Socket Gel Liner from Silipos, handwritten date of Jan. 1, 1995 (Advertisement of Silipos, p. 22).
Zook, Gerald, Soft Viscoelastic Gels: Potentially Valuable Padding and Medicating Materials for Foot Care Products, Current Podiatric Medicine, Oct. 1990, pp. 11-13.
Chadderton, H. Clifford, Silopad Soft Socket Gel Liner, Prosthetics, Fall 1995, pp. 49-50.
Full Potential Newsletter, Current Trends in Prosthetic-Orthotic Rehabilitation, No. 38, 1995, pp. 1-4.

Silipos Prosthetics/Orthotics Catalog, Single & Double Socket Gel Liners, p. 9, vol. II, 1997.
New Introductory Price! Soft Socket Gel-Liner, Silipos Advertisement, unknown date and publication.
ICEROSS, Patient Instructions, DVD, 1993.
Kristinsson, O, The ICEROSS concept: a discussion of a philosophy, Prosthetics and Orthotics International, 1993, vol. 17, pp. 49-55.
Fillauer, Carlton E., Pritham, Charles H., Fillauer, Karl D., Evolution and Development of the Silicone Suction Socket (3S) for Below-Knee Prostheses; JPO 1989, vol. 1, No. 2, p. 92, USA.
Madigan, Robert, M.D., and Fillauer, Karl D., Technique 3-S Prosthesis: A Preliminary Report, JPO, 11:112-117, 1991 Raven Press, Ltd., New York.
Staats, Timothy B., Multiple Durometer Socket Liners for P.T.B. Prostheses, Orthotics and Prosthetics, 1985, The American Orthotic and Prosthetic Association, vol. 38, No. 4, pp. 63-68.
Koch, Richard C. and Sturza, Henry J., Polyvinylchloride Gel in Orthotics and Prosthetics, Part I, Preparation and Application of Silicone Gel, Orthotics and Prosthetics, Sep. 1971, pp. 16-19.
Koepke, George H., Giacinto, Joseph P., and McUmber, Richard A., Polyvinylchloride Gel in Orthotics and Prosthetics, Part II, Silicone Gel Below-Knee Amputation Prostheses, Orthotics and Prosthetics, Sep. 1971, pp. 20-22.
Cluitmans, J., Geboers, M., Deckers, J. and Rings, F., Experiences with respect to the ICEROSS system for trans-tibial prosthesis, Prosthetics and Orthotics International 1994, 18, pp. 78-83.
SiloLiner™ Brochure (4 pp.); Silipos, 7049 Williams Road; L.P.O. Box 211; Niagara Falls, NY 14304; Toll free: 1-800-229-4404.
Luxury Liner Brochure the Maximum Comfort Sleeve (4 pp.); 180 N. San Gabriel Blvd., Pasadena, CA 91107-3488 USA, P.O. Box 5030, Pasadena, CA 91117-0030; www.usms.com; Tel: (818) 796-0477; Fax: (818) 440-9533.
ALPS ClearSheath Silicone Sheaths (1 pp.); Alps South Corp.; 6504 44th Street N., Pinellas Park, FL 34664; Tel: 1-800-574-5426; (813) 528-8566; Fax: (813) 528-8862.
New! The TEC Profile (2 pp.); 820 Sundial Drive, Waite Park, MN 56387; Tel: 320 259-4853; 1-800-688-4832; Fax: (320) 251-0110; www.tecinterface.com.

* cited by examiner

SECTION 2-2

SECTION 6-6

POLYMERIC PROSTHETIC LINER WITH CONTROLLED STRETCH CHARACTERISTICS

TECHNICAL FIELD

The present invention is directed to a fabric-covered polymeric prosthetic liner designed to function as a standalone interface between an amputee's residual limb and the interior of a prosthetic socket. More particularly, the present invention is directed to such a prosthetic liner having limited and controlled longitudinal stretch characteristics.

BACKGROUND

Polymeric prosthetic liners (or "liners") have become the interface of choice among amputees due to various beneficial characteristics thereof. These characteristics include, for example, comfort, security of suspension, protection of the residual limb, and ease of use. Modern liner technology allows amputees to employ a liner as the sole (stand-alone) interface between their residual limb (which is also commonly referred to as a residuum or amputation stump) and the interior of a prosthetic socket—in contrast to known wool or knit socks and cushioned socks or sheaths that must be worn in multiple layers and/or various combinations to provide sufficient cushioning and protection to a residual limb.

Prosthetic liners may be non-suspensory in nature. Non-suspensory liners are commonly referred to as "cushion liners." Prosthetic liners may optionally be suspensory in nature and may, therefore, include a docking element that facilitates suspension by mechanical attachment of the liner to a prosthesis. Suspensory liners are commonly referred to as "locking liners." Liners can be of standard "off-the-shelf" design, meaning the liner is of generic shape and will fit a range of residual limb shapes and sizes. Alternatively, liners may be custom designed for a particular amputee.

Liners may be comprised of various polymeric materials, including silicone, urethane, and thermoplastic elastomers (TPE) gels. Liners are now commonly made using various block copolymer and mineral oil gel compositions. Such polymeric materials, particularly block copolymer and mineral oil gel compositions, have proven themselves to provide an optimal level of comfort for most users.

It is also known to construct such liners with an outer layer of fabric. That is, there exist patented fabric-covered liners having an interior of exposed polymeric gel for contacting and cushioning an amputee's residual limb, and an outer layer of fabric for, among other things, increasing the wear resistance of the liner, and facilitating donning/doffing and insertion of the liner-covered residual limb into a prosthetic socket. Such patented fabric-covered liner products are available from The Ohio Willow Wood Company in Mt. Sterling, Ohio.

While polymeric gel materials provide amputees with a great deal of cushioning and comfort, it is well known that such gels are also highly stretchable. The stretchable nature of such gels allows a liner constructed therewith to conform well to residual limbs of different shape. However, and particularly with respect to locking liners or cushion liners used with vacuum suspension systems, the stretchable nature of these gel materials may allow for the associated liner to stretch to an undesirable degree along the length of the residual limb (i.e., in a longitudinal direction).

To this end, it is desirable to limit the longitudinal stretch of a prosthetic liner. One complicating factor in this regard is that any longitudinal stretch limiting technique employed must not significantly limit the ability of the liner to stretch radially (i.e., circumferentially). Some degree of circumferential stretch is required in order for a liner to accommodate residual limbs of different diameter while still maintaining an intimate fit therewith. Some amount of longitudinal stretch is also required for limb accommodation purposes. Consequently, employing a technique that overly inhibits stretching of a liner in a circumferential direction or that completely prevents stretching of a liner in a longitudinal direction is generally unacceptable.

As would be understood by one of skill in the art, liners as described above are frequently used by lower limb amputees. Lower limb amputees generally fall into one of two categories: above knee (AK) amputees and below knee (BK) amputees. In the case of a BK amputee, the knee joint is still present and, thus, a bending of the residual limb at the knee joint will still occur during ambulation. While the prosthetic hard socket of a BK prosthesis is generally recessed to accommodate the knee joint, BK amputees typically wear a liner that extends over the knee joint to some point along the thigh of the residual limb. Consequently, bending of the knee joint occurs under cover of the liner.

As should be apparent, the use of liners by BK amputees presents yet another problem when attempting to limit the longitudinal stretch of a liner. Particularly, because the knee joint bends while covered by the liner, and because the polymeric gel of the liner clings to the skin of the residual limb, providing a BK amputee with a liner that exhibits no longitudinal elasticity or that has overly limited longitudinal stretch characteristics, can hinder or render uncomfortable bending of the knee joint. This may result from the knee joint struggling to stretch the liner and/or from the polymeric gel material pulling against the skin of the anterior portion of the knee joint. In any event, considerable pressure can be applied to the patellar area of the knee joint if a liner inhibits knee flexion. As would be apparent, a similar problem would exist in the case of a liner that covers the elbow joint of an upper extremity amputee.

Various techniques have been proposed and employed in an attempt to restrict longitudinal liner stretch to an acceptable degree. These techniques have included, without limitation, embedding a reinforcing mesh or wires in the polymeric material at the distal end of the liner, attaching strips of material of limited longitudinal stretch to the exterior of the liner, and covering the entire liner with a material (e.g., fabric) that exhibits no stretch or much less stretch than the polymeric gel portion of the liner. None of these techniques have provided acceptable results. The embedment or attachment of reduced stretch materials to a liner has proven ineffective at controlling the overall longitudinal stretch thereof. Further, known liners having an embedded mesh at the closed end have also exhibited greatly reduced stretch in the radial or circumferential direction. Covering an entire liner with a non-stretch material or a material of greatly reduced stretch is undesirable for the reasons articulated above.

It can be understood from the foregoing discussion that there is a need for a polymeric gel liner that exhibits limited and controlled longitudinal stretch characteristics without adversely affecting other liner characteristics or user comfort. Liners of the present invention satisfy this need.

SUMMARY OF THE OF THE GENERAL INVENTIVE CONCEPT

A liner of the present invention is designed to enclose at least a portion of a residual limb. As such, a liner of the present invention generally includes an open end for allowing introduction of the residual limb, and a closed end opposite the open end. The closed end generally abuts and cushions the distal end of the residual limb when the liner is worn. Such a liner may be used by an upper or lower extremity amputee.

A liner of the present invention is comprised of a polymeric material with a specially designed fabric outer covering. The polymeric material may be, without limitation, silicone, urethane, or a thermoplastic elastomer (TPE). Of particular interest are block copolymer and mineral oil gel compositions, as such materials have proven to be especially effective at cushioning and protecting residual limbs while simultaneously providing amputees with a high level of comfort.

Once constructed, a liner of the present invention includes a polymeric material interior and a fabric exterior. When used with a prosthesis, the polymeric material of the liner interior is in contact with the skin of a residual limb and the fabric exterior is in contact with the interior of a prosthetic socket.

Because the polymeric material of the liner interior will be in contact with the skin of a residual limb when the liner is worn, the polymeric material is generally smooth and continuous in nature such there are no seams or other discontinuities that may cause amputee discomfort. A liner of the present invention will typically protect and cushion the entire portion of a residual limb residing in a prosthetic socket.

While a liner of the present invention may be of the cushioning liner variety, other embodiments are constructed as locking liners. To this end, a liner of the present invention may include a docking element at the closed end for facilitating connection of the liner to the socket of a prosthetic limb. Such docking elements may be designed with a special accordion shape that provides for increased comfort when the liner is worn by better conforming to the distal shape of the residual limb.

The longitudinal stretch (elasticity) of a liner of the present invention is controlled primarily by its fabric exterior. More particularly, the longitudinal elasticity of a liner of the present invention is controlled by both the elasticity characteristics of the fabric materials that cover the liner exterior, as well as the location and arrangement of those fabric materials. Even more particularly, a liner of the present invention is covered with more than one fabric material, each fabric material having a particular stretch characteristic. These fabric materials form particular sections of the liner, and are sized and arranged to most effectively limit longitudinal elasticity while simultaneously permitting adequate radial elasticity, knee flexion (in the case of a BK liner), and elbow flexion (in the case of a liner for use with an arm prosthesis).

Manipulating the physical properties of the polymeric material portion of a liner of the present invention may also be used to assist with controlling longitudinal liner stretching. That is, in conjunction with the use of a stretch-controlling fabric as described above, the polymeric material itself may also be rendered less stretchable, such as by reducing the amount of mineral oil and/or other plasticizer(s) present therein and/or by adding a reinforcing material such as KEVLAR thereto.

A better understanding of a liner of the present invention can be gained by review of the following description of several exemplary embodiments thereof, along with the associated accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1b is a rear view of the liner of FIG. 1a;

FIG. 5b is a rear view of the liner of FIG. 5a;

DETAILED DESCRIPTION OF THE EXEMPLARY EMBODIMENT(S)

Exemplary embodiments of a controlled-stretch prosthetic liner of the present invention are described below. These exemplary embodiments are provided solely for the purpose of illustration, and not limitation. As described above, each embodiment includes an inner layer of polymeric material and an outer layer of fabric. With respect to the cross-sectional views illustrated herein, it should be noted that the thickness of the fabric layers and the polymeric material layers has been exaggerated for clarity. Further, the fabric layers and polymeric material layers are not necessarily drawn to scale with respect to each other.

Figure 1A:
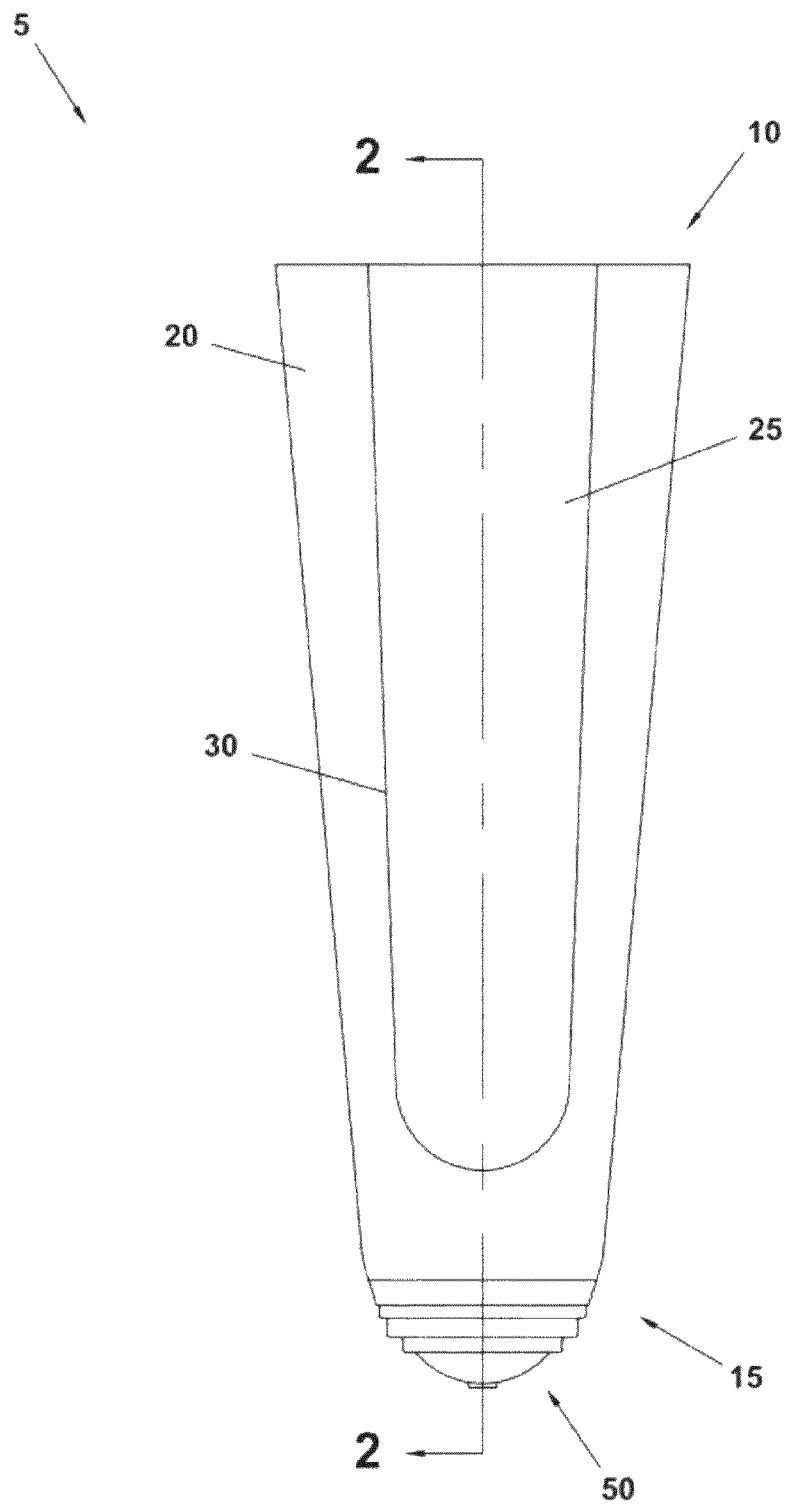
FIG. 1a is a front view of one exemplary embodiment of a controlled-stretch prosthetic liner of the present invention.
Figure 1B:
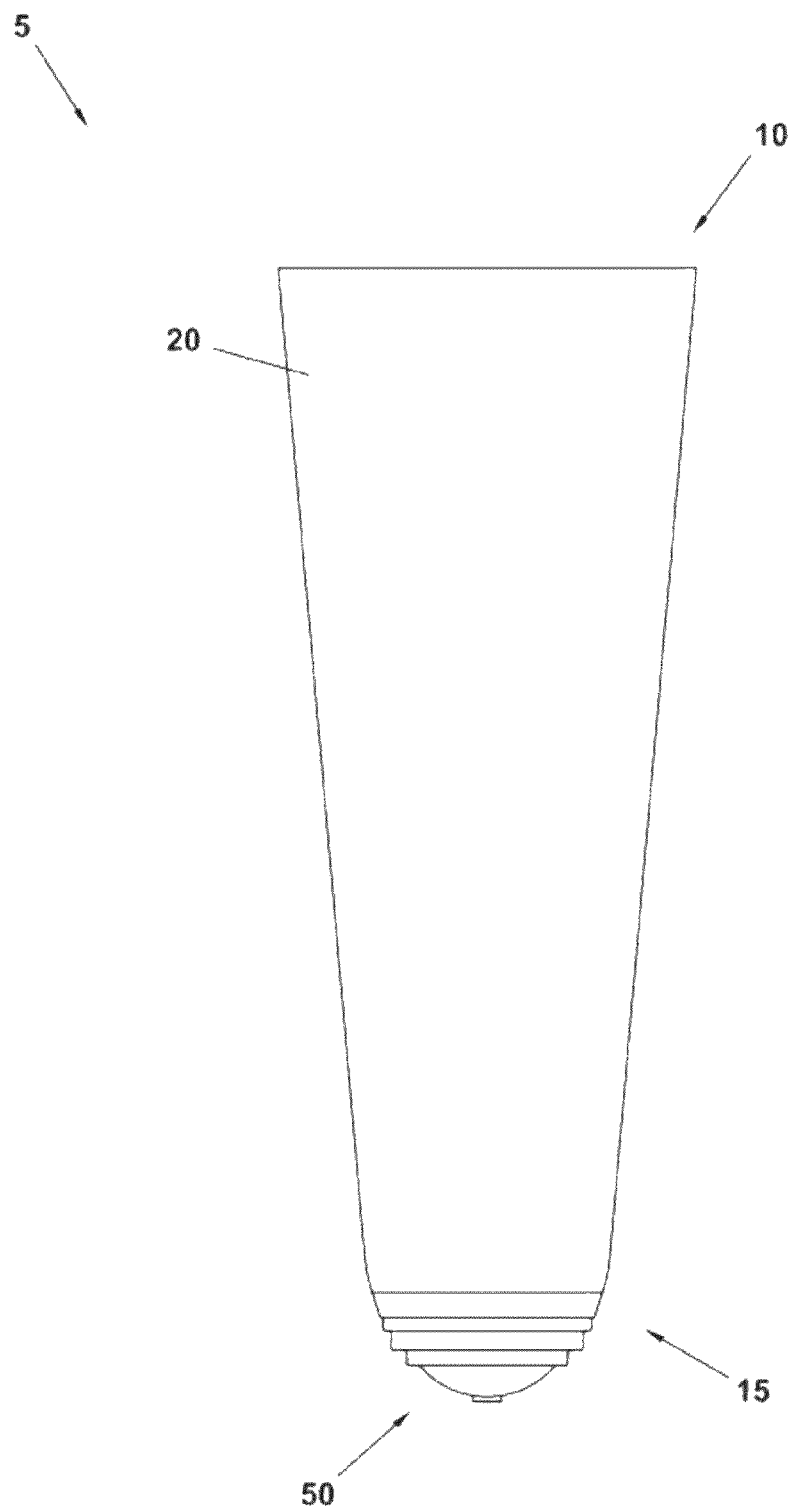
Figure 2:
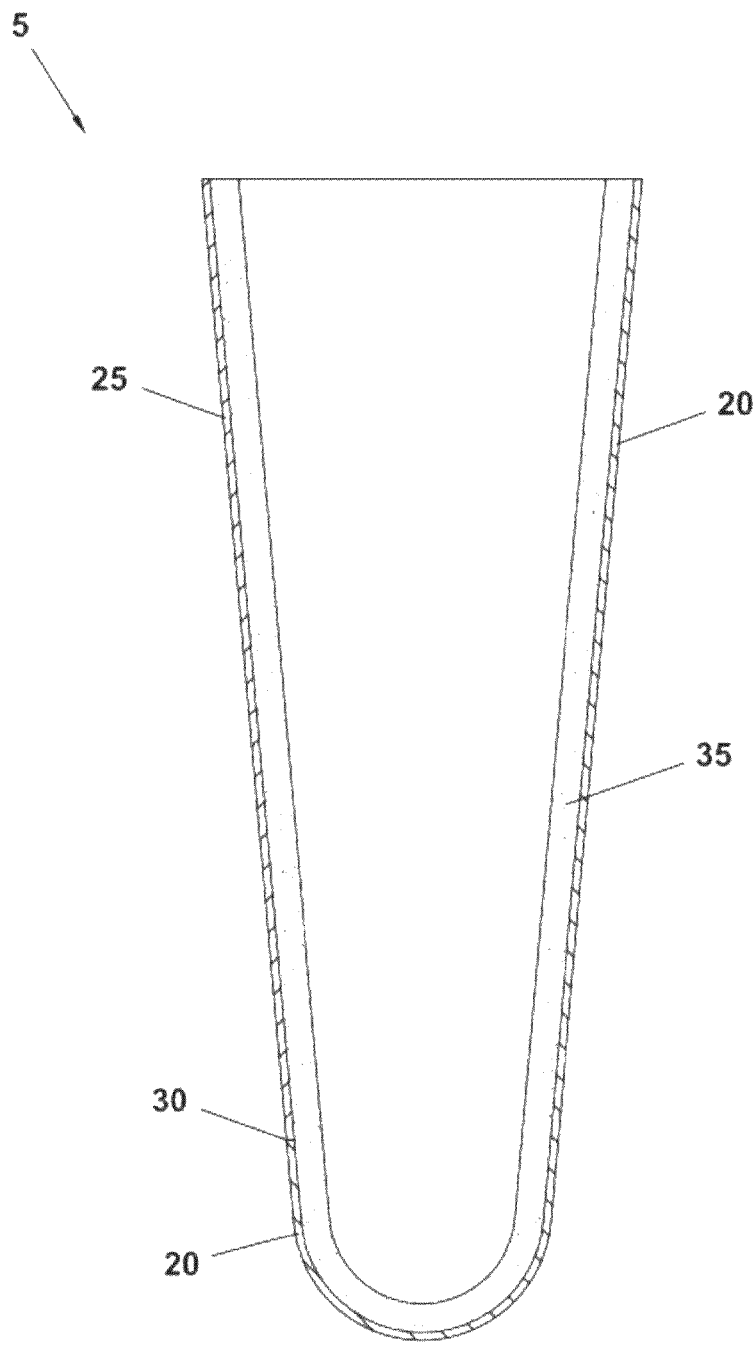
FIG. 2 is a cross-sectional view taken along line 2-2 of the liner of FIG. 1a, wherein the docking element shown therein has been removed for clarity.

A first embodiment of a below knee (BK) controlled-stretch prosthetic liner (hereinafter "liner") 5 of the present invention is depicted in FIGS. 1a-1b and FIG. 2. As shown, the liner 5 includes an open end for permitting insertion of a residual leg, and a closed end 15 opposite the open end.

As can be best observed in FIG. 2, the interior of the liner 5 is comprised of a polymeric material 35 while the exterior of the liner is comprised of fabric 20, 25. The polymeric material 35 of the liner interior will be in contact with the skin of a residual limb when the liner is worn. The fabric portions 20, 25 of the liner exterior are arranged to be in contact with the interior of a prosthetic socket when the liner is used with a prosthetic limb.

Because the polymeric material of the liner interior will be in contact with the skin of a residual limb when the liner is worn, the polymeric material is generally smooth and continuous in nature such there are no seams or other discontinuities that may cause amputee discomfort. Typically, the polymeric material will extend completely to the edge of the fabric at the open end of the liner, such that the entire interior surface of the fabric is covered therewith. Alternatively, it is also possible that some length of fabric may remain devoid of polymeric material so as to form a band or cuff of fabric at the open end of the liner. It is preferred, however, that the polymeric material extend along the fabric to a length that is at least equivalent to the depth of a prosthetic socket cavity with which the liner will be used. Consequently, a liner of the present invention will protect and cushion the entire portion of a residual limb residing in a prosthetic socket.

As can be best observed in FIGS. 1a-1b, the liner 5 includes a fabric covering having two distinct fabric sections 20, 25. The larger fabric section 20 is comprised of a stretch-controlling fabric that is used to control the overall longitudinal elasticity of the liner 5. This stretch-controlling fabric section 20 covers a majority of the liner exterior, except for the two-way stretch knee panel 25 shown in FIG. 1a. Because this particular liner 5 is a BK liner, the knee panel 25 is included to allow for proper flexion of the amputee's knee joint when wearing the liner. The knee panel section 25 and the stretch-controlling fabric section 20 are joined at a seam 30, which is typically a sewn seam.

Stretch-controlling fabrics, as such terminology is used herein, refers to fabrics that are much more stretchable in one direction than the other. That is, a stretch-controlling fabric has a limited stretch direction and a non-limited stretch direction. Particularly, when used in a liner of the present invention, such stretch-controlling fabrics are oriented to permit considerably greater stretch in a circumferential direction than in a longitudinal direction (i.e., along the length of the liner). Such asymmetric stretch characteristics result from the specific materials used to construct the stretch-controlling fabric, the percentages of the materials used, and the way in which those materials are assembled to form the fabric. A great deal of research and testing has been undertaken in order to determine the various ideal stretch-controlling fabric parameters.

Based on mechanical testing data and data obtained from on-patient testing of prototype liners, it has been determined that a stretch-controlling fabric of the present invention preferably has a range of elasticity of between about 10-40% in the limited-stretch direction. More preferably, the elasticity of a stretch-controlling fabric of the present invention is less than about 30% in the limited stretch direction. Concurrently, a stretch-controlling fabric of the present invention preferably has a range of elasticity of between about 70-250% in the non-limited stretch direction. More preferably, a stretch-controlling fabric of the present invention preferably has a range of elasticity of between about 140-190% in the non-limited stretch direction. In one particular example of such a stretch-controlling fabric, elasticity in the limited stretch direction is about 17.7% and elasticity in the non-limited stretch direction is about 165%.

As mentioned above, it is desired that a given liner of the present invention is able to fit a range of residual limb sizes. Because residual limbs of different patients will typically have different circumferences, it is desired that a liner of the present invention be able to sufficiently expand (stretch) circumferentially so as to accommodate these varying limb dimensions. Therefore, when constructing a liner according to the present invention, it is also important to ensure that the liner provides an intimate fit with the residual limb without being so constrictive (tight) as to result in discomfort or to act as a stump shrinker. To this end, other properties of stretch-controlling fabrics should also be considered.

With respect to tightness, consideration should also be given to the modulus of the stretch-controlling fabric. Preferably, a stretch-controlling fabric of the present invention has a 50% modulus of between about 0.5-12.0 lbf. in the non-limited stretch direction. More preferably, a stretch-controlling fabric of the present invention has a 50% modulus of between about 0.5-2.0 lbf. in the non-limited stretch direction. Good comfort was reported when amputees tested a prototype liner of the present invention having a stretch-controlling fabric with a 50% modulus of 1.0 lbf. in the non-limited stretch direction.

With respect to liner properties such as, without limitation, abrasion resistance and polymeric material thickness, it is advisable to also consider the weight of the stretch-controlling fabric. It has been found through significant testing that the weight of a stretch-controlling fabric of the present invention should preferably be between about 7-26 oz./sq. yd. More particularly, the weight of a stretch-controlling fabric of the present invention should be between about 12-22 oz./sq. yd. Good results have been achieved when constructing and testing prototype liners according to the present invention using a stretch-controlling fabric having a weight of approximately 21 oz./sq. yd.

Because the knee panel 25 is provided to allow for proper flexion of a residual limb knee joint when the liner 5 is worn, the fabric of the knee panel preferably exhibits two-way stretch (i.e., significant elasticity in both the longitudinal and radial directions). Based on mechanical testing data and data obtained from on-patient testing of prototype liners, it has been determined that a knee panel fabric of the present invention preferably has a range of elasticity of between about 70-250% in both the longitudinal and radial directions. More preferably, the elasticity of a knee panel fabric of the present invention is between about 100-130% in both the longitudinal and radial directions. In one particular example of such a knee panel fabric, elasticity in both directions is approximately 115%.[1] In other embodiments of a liner of the present invention, such a two-way stretch fabric may exhibit significant, but unequal, elasticity in both the longitudinal and radial directions

[1] The preferred elasticity value ranges provided herein for both a stretch-controlling fabric and a knee panel (two-way stretch) fabric were determined in accordance with ASTM D4964-96 (2008)e1—Standard Test Method for Tension and Elongation of Elastic Fabrics (Constant-Rate-of-Extension Type Tensile Testing Machine). Testing was conducted by subjecting 3 inch wide, 10 inch circumference looped samples to a 20 lb. load. The samples were cycled three times, with the stretch data taken on the third cycle and the modulus determined on the third outgoing cycle (i.e., at the return of the third cycle).

As with a stretch-controlling fabric used in the present invention, the modulus of a knee panel fabric should also be considered. Preferably, a knee panel fabric of the present invention has a 50% modulus of between about 0.9-11.25 lbf. in both directions. Knee panel fabrics having a nominal 50% modulus of at least about 3.25 lbf. in both directions have produced good results in testing.

The thickness of a knee panel fabric of the present invention liner should be controlled for the same or similar reasons discussed above with respect to a stretch-controlling fabric used in the present invention. It has been found through significant testing that the weight of a knee panel fabric of the present invention should preferably be between about 6-27 oz./sq. yd. More particularly, the weight of a knee panel fabric of the present invention should be between about 12-22 oz./sq. yd. Good results have been achieved when constructing and testing prototype liners according to the present invention using a knee panel fabric having a weight of approximately 16 oz./sq. yd.

Based on the physical properties and related performance characteristics thereof, various acceptable stretch-controlling fabric materials and two-way stretch fabric materials have been identified. Acceptable stretch-controlling fabric materials may include, without limitation, fabric having a rib knit (e.g., 1×1 rib knit) construction using one or a combination of CORDURA (Nylon 6,6), Taslan nylon, Stretch nylon, Spun Nylon, Polyester, and CELLIANT. It has been determined through testing that a material comprising a CORDURA/Nylon blend may perform particularly well when used for such a purpose. A more particular CORDURA/Nylon blend that has performed particularly well in testing when used as a stretch-controlling fabric includes approximately 54% CORDURA, approximately 37% Stretch Nylon, and approximately 9% elastic. In one exemplary embodiment of such a material, the CORDURA count is 1/160, the Stretch Nylon count is 2/100, and the elastic cord is 1 M.

Acceptable two-way stretch fabric materials may include, without limitation, fabrics which exhibit sufficient elasticity in both directions, as well as high wear resistance and high bond strength to the polymeric material being used. Preferred fabrics include nylon/spandex fabrics and, more preferably, stretchable non-woven fabrics, such as the line of WEARFORCE fabrics from Xymid, LLC in Midlothian, Va. that connect bulkable yarns with non-woven sheet substrates in a warp-knit construction.

As mentioned briefly above, it has been determined that the elasticity limiting characteristics of a stretch-controlling fabric used in the present invention may be controlled or enhanced by employing particular fabric manufacturing techniques. One such technique is to manufacture the stretch-controlling fabric with ribbing. Wikipedia offers the following general information regarding "ribbing":

In knitting, ribbing is a pattern in which vertical stripes of stockinette stitch alternate with vertical stripes of reverse stockinette stitch. These two types of stripes may be separated by other stripes in which knit and purl stitches alternate vertically. The number of knit and purl stripes (wales) are generally equal, although they need not be. Ribbing is notated by (number of knit stitches)×(number of purl stitches). Thus, 1×1 ribbing has one knit stitch, followed by one purl stitch, followed by one knit stitch, and so on. Ribbing has a strong tendency to contract laterally, forming small pleats in which the purl stitches recede and the knit stitches come forward. Thus, ribbing is often used for cuffs, sweater hems and, more generally, any edge that should be form-fitting The elasticity depends on the number of knit/purl transitions; 1×1 ribbing is more elastic than 2×2 ribbing, etc.

Additional and more detailed information regarding ribbing may be found, for example, in *Flat Knitting Technology*, by Dr. Samuel Raz, printed by C. F. Rees GmbH, ©1993; and *Knitting Technology—A Comprehensive Handbook And Practical Guide*, Third Edition, by David J. Spencer, Woodhead Publishing.

It has been found that when a ribbed stretch-controlling fabric is used in a liner of the present invention, its elasticity may be manipulated by inserting an elastic cord in the courses of the ribbing. More particularly, elastic cord may be inserted ("laid-in") every course, or every 2, 3, or 4 courses, etc., of the stretch-controlling fabric. The elastic material used may be synthetic elastic (such as Spandex, Lycra, or Elastane) or natural rubber elastic (such as Latex), or a combination thereof. By adjusting the type, size, and spacing of the elastic cord placed in the fabric, the modulus of the fabric can be adjusted for optimal performance and comfort. In this regard, the 50% modulus of such an enhanced fabric is preferably between about 0.5-2.2 lbf. in the non-limited stretch direction and, more preferably, between about 0.8-1.8 lbf. in the non-limited stretch direction. It is believed that this construction technique imparts unique stretch characteristics to such a fabric, and that no such fabric has ever been used in the manufacture of a prosthetic liner.

With further respect to the use of ribbing, it has been determined that a plaiting method may also be employed to control what material are is most prominent on a given surface of the fabric. More specifically, a ribbed fabric can be provided with a type of fiber on its interior surface that will promote good bonding to the polymeric material of a liner. Simultaneously, such a fabric may be provided with a fiber of a different type on its exterior, which fiber type may be selected based on its ability to provide for abrasion resistance and increased durability, and/or because it exhibits a soft or slick hand that would facilitate insertion of a liner into a prosthetic socket.

As should be apparent based on the foregoing description, a BK liner of the present invention should be constructed in a manner that acceptably limits its longitudinal stretch while not adversely affecting knee flexion. To this end, it has been found that in addition to employing fabrics having the various aforementioned characteristics, the length and width of the two-way stretch knee panel also contributes to the overall effectiveness of the liner.

It was previously mentioned that amputees may have residual limbs of different size. In addition to differences in circumference, the length of the residual limb may also vary. For example, in the case of a BK amputee, the length of the residual limb portion extending from the knee joint to the distal end of the residual limb may vary considerably. It was also previously mentioned that liners of the present invention can be of standard "off-the-shelf" design, or may be custom designed for a particular amputee. When a liner of the present invention is a custom liner, the overall dimensions of the liner and of the knee panel may be selected to best accommodate the residual limb of interest. However, when a liner of the present invention is of the off-the-shelf variety, the overall dimensions of the liner and of the knee panel are preferably selected to fit a range of residual limb sizes.

In order to best control longitudinal elasticity, it is preferred that the stretch-controlling fabric located along the anterior of a BK liner of the present invention extend from the distal end as far as possible toward the knee joint without interfering with knee flexion (see e.g., FIG. 1a). After analyzing data associated with a significant number of different BK residual limbs, it has been determined that when a liner of the present invention is a BK custom liner, the distance from the distal end of the liner to the distal end (beginning) of the knee panel should typically be between about 2-12 inches. However, the precise distance will generally be determined by the dimensions of the particular residual limb for which the liner is designed. When a liner of the present invention is an off-the-shelf BK liner, it has been determined that the longitudinal distance from the distal end of the liner to the distal end (beginning) of the knee panel should generally be about 4 inches. The aforementioned analysis of residual limb dimensions indicates that this 4 inch distance should be appropriate for approximately 90% of the BK amputee population. That is, providing about 4 inches of stretch-controlling fabric below the distal end of the knee panel will result in adequate stretch reducing properties and proper knee flexion for approximately 90% of the BK amputee population.

As with the length of the knee panel, the width of the knee panel in a BK liner should be sufficient to permit proper knee flexion. Obviously, the maximum width of the knee panel will be limited by the width of the anterior portion of the fabric pattern used to create the liner. It has been determined, however, that for an off-the-shelf BK liner, a knee panel width range of approximately 1.5-8.0 inches and, more particularly 1.8-3.8 inches, taken at the tangent point (i.e., the seam) of the panel and the stretch-controlling fabric, is appropriate for the majority of BK amputees. Alternatively expressed, the width of a knee panel of the present invention may range from between about 40-100% of the full lay-flat width of the associated liner measured at the tangent point of the panel and the stretch-controlling fabric.

Various polymeric materials described above may comprise the polymeric portion of a liner of the present invention. For example, the polymeric material of the particular exemplary liner 5 shown and described herein is a block copolymer and mineral oil gel composition. Such materials have proven particularly effective at cushioning and protecting a residual limb when used in a liner.

Manipulating the physical properties of the polymeric material portion of a liner of the present invention may also be used to assist with controlling longitudinal liner elasticity. Particularly, the polymeric material itself may also be rendered less stretchable by adding a reinforcing material. One such acceptable reinforcing material is KEVLAR, which may be added in the form of, without limitation, pulped fibers, flocked fibers, short and long fiber strands, powders and nano-sized particles (e.g., nano-clay particles).

In lieu of or in addition to the use of a reinforcing material, the polymeric material may be of a composition having a less than typical percentage of plasticizer(s) present therein. For example, when the polymeric material is a block copolymer and mineral oil composition, the typical percentage of mineral oil may be reduced. In one particular example of such a composition, the block copolymer is a styrene-ethylene-ethylene-propylene-styrene (SEEPS) block copolymer, and the mineral oil content constitutes approximately 81.5% by weight of the overall composition.

Figure 3:
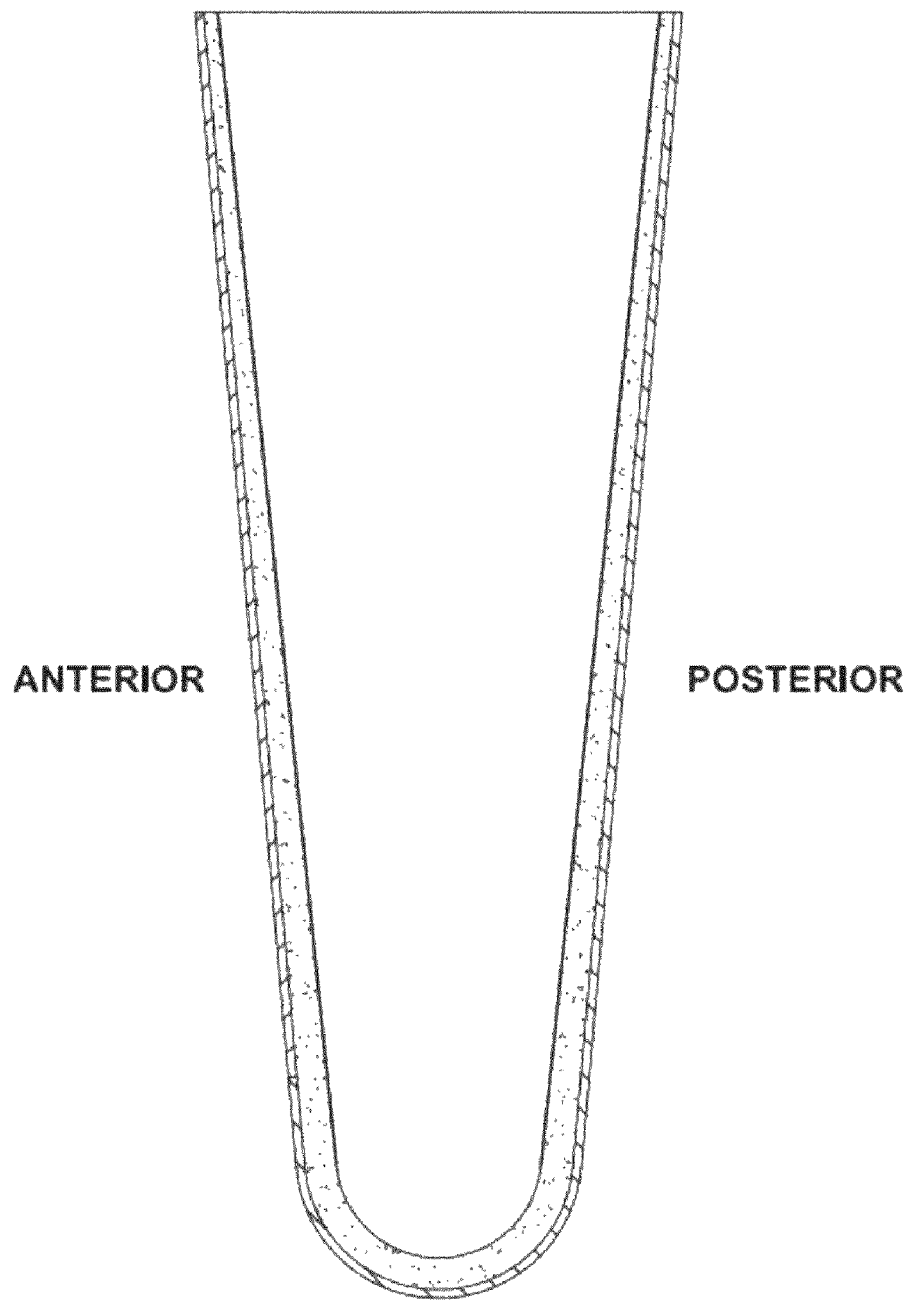
FIG. 3 is a cross sectional view of a controlled-stretch prosthetic liner of the present invention having a symmetric polymeric material distribution.
Figure 4:
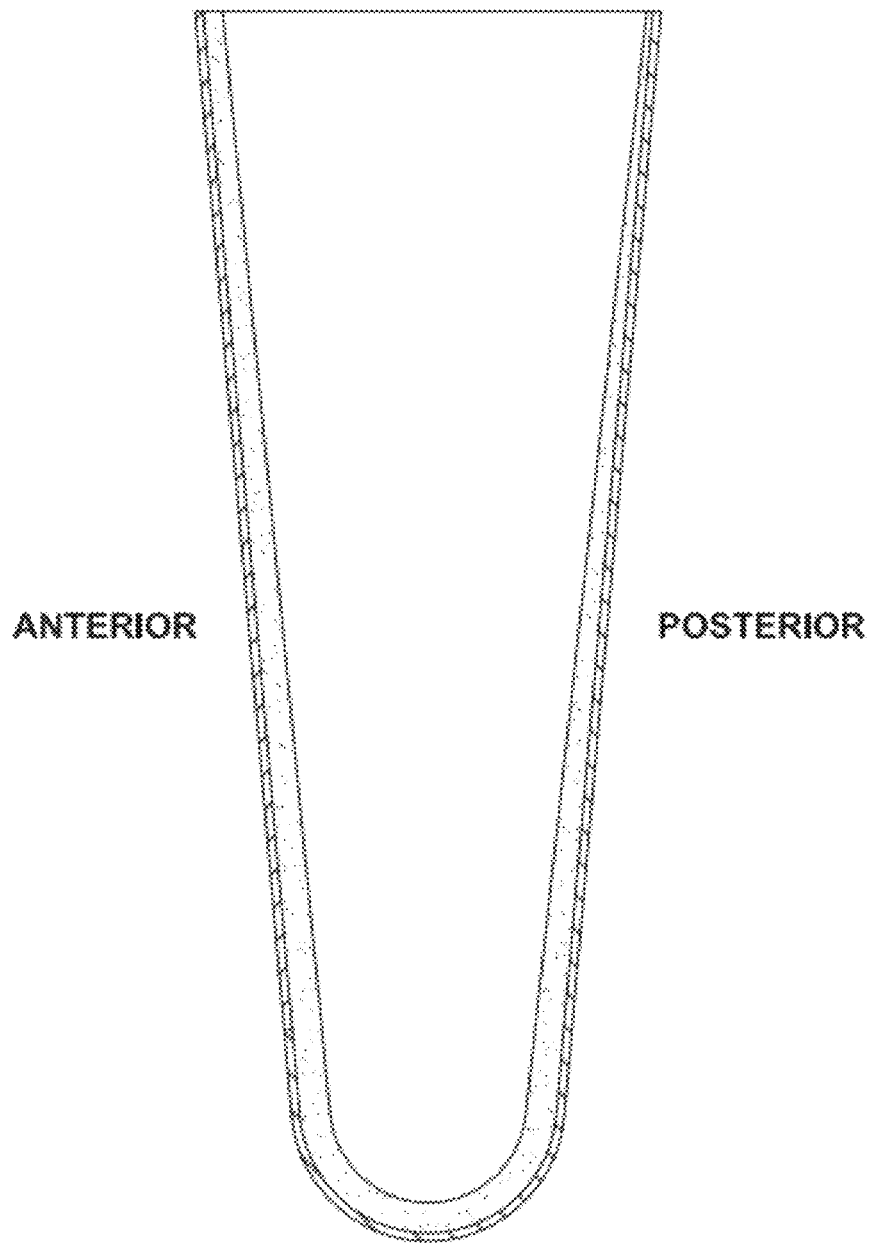
FIG. 4 is a cross sectional view of a controlled-stretch prosthetic liner of the present invention having an asymmetric polymeric material distribution.

In order to best maximize amputee comfort, it is preferred, but not essential, that the polymeric material tapers in thickness from a thicker area at the closed end of the liner to a thinner area at the open end (see FIGS. 3-4). The polymeric material surrounding the closed end of the liner may be between about 5-15 millimeters in thickness and, more preferably, is between about 6-10 millimeters in thickness. However, the thickness of the polymeric material provided in a particular liner of the present invention may be adjusted to account for particular residual limb shapes, abnormalities, etc. and, therefore, may fall outside of this typical thickness range. Preferably, the polymeric material tapers to a thickness of between about 1.5-5.0 millimeters at or prior to the open end of the liner.

While the polymeric material of a liner of the present invention may taper symmetrically in thickness from the closed end to the open end as depicted in FIG. 3, it is preferred, but not essential, that the thickness of the polymeric material tapers in an asymmetric manner (as shown in FIG. 4). More specifically, it is preferred that at a given distance from the distal end of the liner, the polymeric material along a front (anterior) portion of the liner be thicker than the polymeric material located along a rear (posterior) portion of the liner. Such an asymmetric taper may be achieved in various ways, such as by tapering the polymeric material along the liner anterior at a reduced angle in comparison to the angle of taper present along the liner posterior. Alternatively, extending the full thickness of the polymeric material along the liner anterior farther toward the open end of the liner before the taper begins may also provide an acceptable solution. In any event, the posterior portion of such a liner will generally have an extended thinned section of polymeric material in comparison to the anterior portion of the liner.

Figures 9A, 9B:
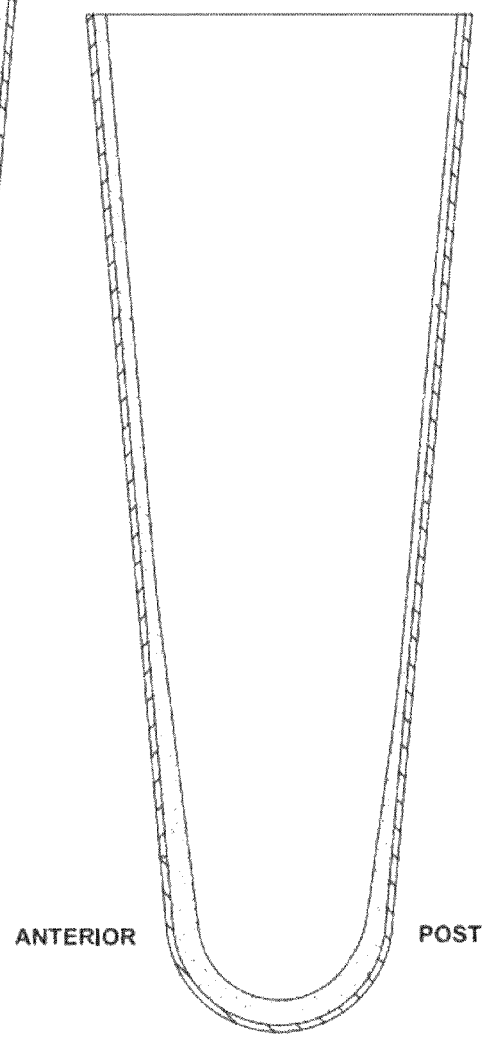
FIG. 9a is a cross sectional view of a controlled-stretch prosthetic liner of the present invention having a symmetric polymeric material distribution that is thickest near the closed end, tapers to a lesser thickness at some point between the closed end and open end, and remains at this reduced thickness to the open end of the liner.
FIG. 9b is a cross sectional view of a controlled-stretch prosthetic liner of the present invention having an asymmetric polymeric material distribution that is thickest near the closed end, tapers to a lesser thickness at some point between the closed end and open end, and remains at this reduced thickness to the open end of the liner.

In certain embodiments of a liner of the present invention, the polymeric material thickness may taper uniformly from a greater thickness near the closed end to a lesser thickness at the open end of the liner. In other embodiments of a liner of the present invention, the polymeric material thickness may taper from a greater thickness near the closed end to a lesser thickness at some point between the closed and open end, and remain at this reduced thickness to the open end of the liner (see FIG. 9). In this latter case, the polymeric material of a liner with a symmetric polymeric material distribution may reach its thinnest point at between about 2-14 inches from the closed (outside) end of the liner, while the polymeric material of a liner with an asymmetric polymeric material distribution may reach its thinnest anterior point at between about 6-20 inches and its thinnest posterior point at between about 3-17 inches from the closed (outside) end of the liner. These dimensions may vary, in part, depending on the overall length of the liner. In order to accommodate amputees of varying size and age, it is contemplated that an off-the-shelf controlled-stretch liner of the present invention may have an overall length of between about 5-24 inches. More commonly, however, an off-the-shelf controlled-stretch liner of the present invention will have an overall length of between about 16-22 inches.

In one exemplary embodiment of a liner of the present invention with an asymmetric polymeric material thickness distribution, the polymeric material tapers from a thickness of approximately 9 millimeters at the closed end to a thickness of approximately 3.75 millimeters. The 3.75 millimeter thickness is reached at a point approximately 10.5 inches from the open end along the anterior side of the liner and a point approximately 6.9 inches from the open end along the posterior side of the liner. The polymeric material thereafter remains approximately 3.75 millimeters thick to the closed end of the liner. In an alternative exemplary embodiment of a liner of the present invention having a symmetric polymeric material thickness distribution, the polymeric material tapers from a thickness of approximately 9 millimeters at the closed end to a thickness of approximately 3.75 millimeters at a point approximately 9.5 inches from the closed (outside) end, and remains approximately 3.75 millimeters thick to the closed end of the liner.

Based on the desired characteristics of a liner of the present invention and on the materials identified above as being suitable for the construction thereof, it is believed that a liner of the present invention should exhibit certain overall characteristics in order to acceptably limit longitudinal stretch while permitting adequate circumferential stretch and providing amputee comfort. Particularly, it has been found that a controlled-stretch portion of a liner of the present invention should exhibit an elasticity in the longitudinal direction of between about 15-25%, an elasticity in the circumferential (non-limited stretch) direction of between about 90-130%, and should have a 50% modulus in the circumferential direction of between about 1.0-2.0 lbf. When the liner is, for example, a BK liner (or an upper extremity liner that will cover an amputee's elbow), the liner should also employ a properly located panel of two-way stretch fabric that exhibits an elasticity of 60% or greater in both the longitudinal and circumferential directions, and has a 50% modulus of between about 1.0-3.0 lbf. As determined through mechanical testing and from test patient feedback, a liner with the above characteristics will provide proper support while imparting a snug, secure feeling without being overly restrictive and uncomfortable.

A collection of test data appears in Table I, below. This test data shows that a liner constructed according to the present invention will possess the physical properties described above. In Table I, liners manufactured according to the present invention are listed as "OWW Select" Liners, with OWW designating The Ohio Willow Wood Company.

All of the products in Table I were tested for longitudinal and circumferential elongation (designated as "L" and "C", respectively), as well as for 50% modulus. The average values obtained for these measurements are shown. Aside from the OWW Select Liners, the remaining liners, sheaths and cushioned socks of Table I are representative of products available from various other prosthetic manufacturers. Other OWW liners are also listed for comparison.

tensile force of 5 lbs. thereto. Stretch and modulus data was collected on the third outgoing cycle.

In reviewing Table I, it will be understood by one of skill in the art that liners of the present invention (i.e., the Select Liners) exhibit characteristics that are superior to other known interface products. For example, while certain known liners and similar products may exhibit a desirable degree of elasticity in a longitudinal direction, such comes at the expense of undesirably or unacceptably low elasticity in the circumferential direction. Certain other tested interface products may exhibit an acceptable degree of longitudinal elasticity at the limited location of a special low stretch matrix or strip of material, but the remainder of the product continues to suffer from an unacceptably high level of longitudinal elasticity. Still other products, such as the Iceross TF Liner, exhibit reduced stretch throughout the entire liner, thereby being subject to the above-described problems with inadequate knee flexion. Based on patient feedback, it has been

TABLE I

| SPECIMEN NAME | STRETCH DIRECTION | AVERAGE STRETCH (%) | 50% MODULUS (lbf.) |
|---|---|---|---|
| OWW Select Liner (w/Standard Gel) | C | 104.35 | 1.52 |
| OWW Select Liner (w/Standard Gel) | L | 20.88 | — |
| OWW Select Liner (w/Hybrid Gel) | C | 112.67 | 1.31 |
| OWW Select Liner (w/Hybrid Gel) | L | 19.99 | — |
| Otto Bock Dermaseal | C | 128.34 | 0.51 |
| Otto Bock Dermaseal | L | 56.93 | 3.38 |
| Alps EZ Liner | C | 162.43 | 1.05 |
| Alps EZ Liner | L | 124.93 | 1.13 |
| Alps EZ Liner (at matrix) | C | 43.88 | — |
| Alps EZ Liner (at matrix) | L | 27.88 | — |
| Ossur Dermo Liner | C | 86.35 | 1.98 |
| Ossur Dermo Liner | L | 40.66 | — |
| Ossur Dermo Liner (at matrix) | C | 69.14 | 2.88 |
| Ossur Dermo Liner (at matrix) | L | 30.86 | — |
| Streifeneder Contex Liner | C | 117.73 | 1.72 |
| Streifeneder Contex Liner | L | 60.13 | 3.59 |
| Streifeneder Contex Liner (at matrix) | C | 91.86 | 2.26 |
| Streifeneder Contex Liner (at matrix) | L | 20.81 | — |
| Otto Bock Adapt Liner | C | 101.33 | 1.63 |
| Otto Bock Adapt Liner | L | 6.94 | — |
| Iceross TF Liner | C | 144.09 | 1.22 |
| Iceross TF Liner | L | 21.59 | — |
| Ossur Synergy Liner | C | 101.19 | 1.73 |
| Ossur Synergy Liner | L | 53.21 | 4.44 |
| Ossur Synergy Liner (at matrix) | C | 58.93 | 4.09 |
| Ossur Synergy Liner (at matrix) | L | 20.66 | — |
| Alps EZFlex Liner (anterior) | C | 200.6 | 1.07 |
| Alps EZFlex Liner (anterior) | L | 142.88 | 1.06 |
| Alps EZFlex (Liner posterior) | C | 235.49 | 0.97 |
| Alps EZFlex Liner (posterior) | L | 37.19 | — |
| Alps EZFlex Liner (anterior, at matrix) | C | 44.66 | — |
| Alps EZFlex Liner (anterior, at matrix) | L | 36.26 | — |
| Alps EZFlex Liner (posterior, at matrix) | L | 20.48 | — |
| OWW Original Liner (FT) | C | 57.11 | 3.82 |
| OWW Original Liner (FT) | L | 32.21 | — |
| OWW Spirit Liner | C | 70.34 | 3.03 |
| OWW Spirit Liner | L | 35.52 | — |
| OWW Max2 Liner | C | 100.18 | 2.11 |
| OWW Max2 Liner | L | 34.45 | — |
| Silipos Low Activity Liner | C | 106.08 | 1.57 |
| Silipos Low Activity Liner | L | 59.72 | 3.02 |
| Silipos Low Activity Liner (at matrix) | L | 19.27 | — |
| Daw Cool Liner | C | 83.72 | 2.56 |
| Daw Cool Liner | L | 54.85 | 3.86 |
| Daw Cool Liner (at no-stretch strip) | L | 11.67 | — |
| Silipos Single Socket Gel Liner | C | 157.89 | 0.63 |
| Silipos Single Socket Gel Liner | L | 189.83 | 0.58 |

Stretch testing of the products listed in Table I was conducted by cutting 1.5 inch by 4 inch samples from each product as indicated, clamping each sample in a tensile testing machine at a grip separation of 2.5 inches and applying a determined that excessive limitations on longitudinal elasticity are also undesirable. Thus, certain known liners also suffer from this drawback (e.g., the Otto Bock Adapt Liner). Many of the listed liners also rely on a matrix or similar arrangement of specialized low-stretch material that must be embedded in the polymeric material, thereby complicating manufacturing.

Figure 5A:
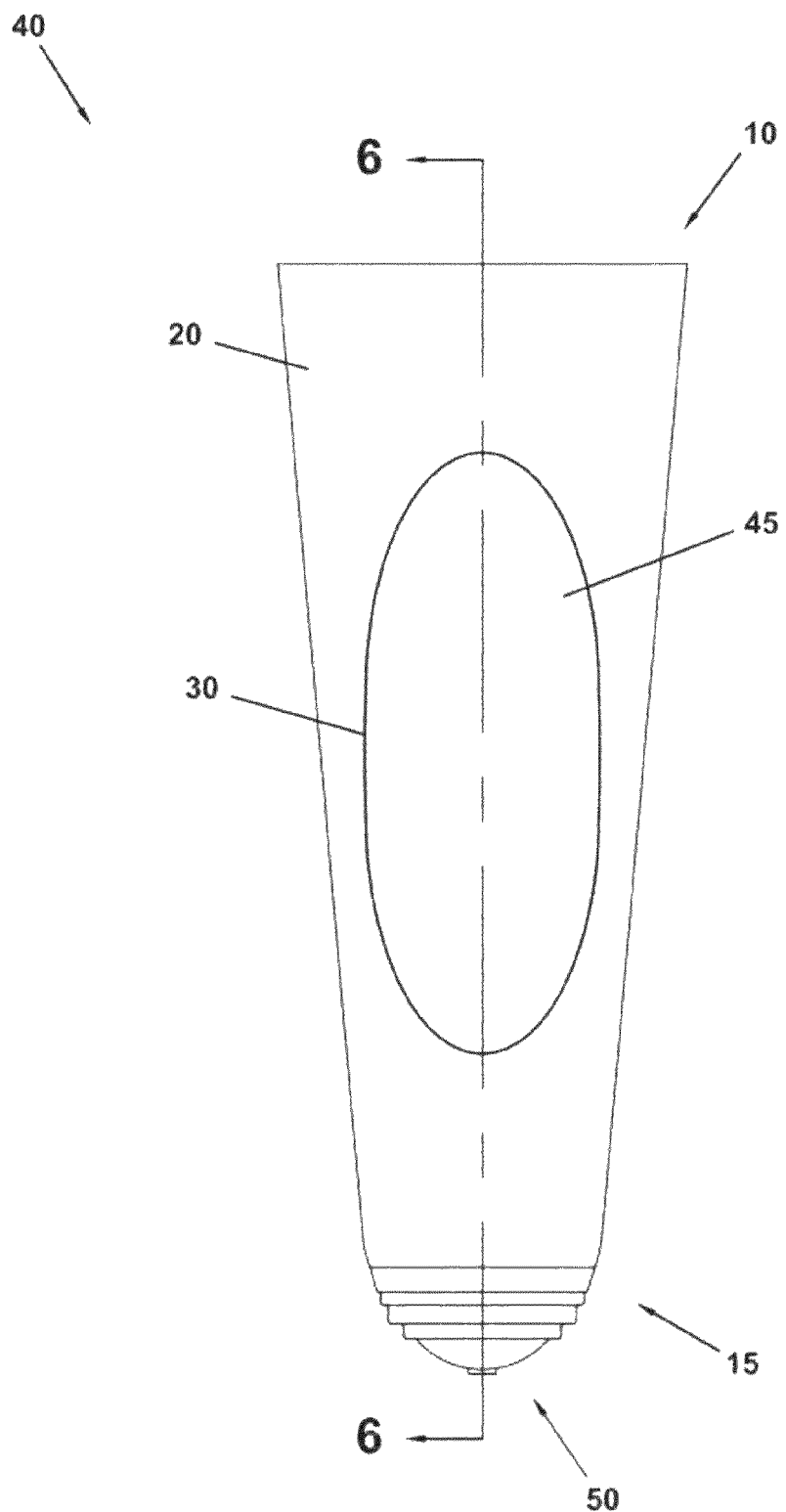
FIG. 5a is a front view of another exemplary embodiment of a controlled-stretch prosthetic liner of the present invention.
Figure 5B:
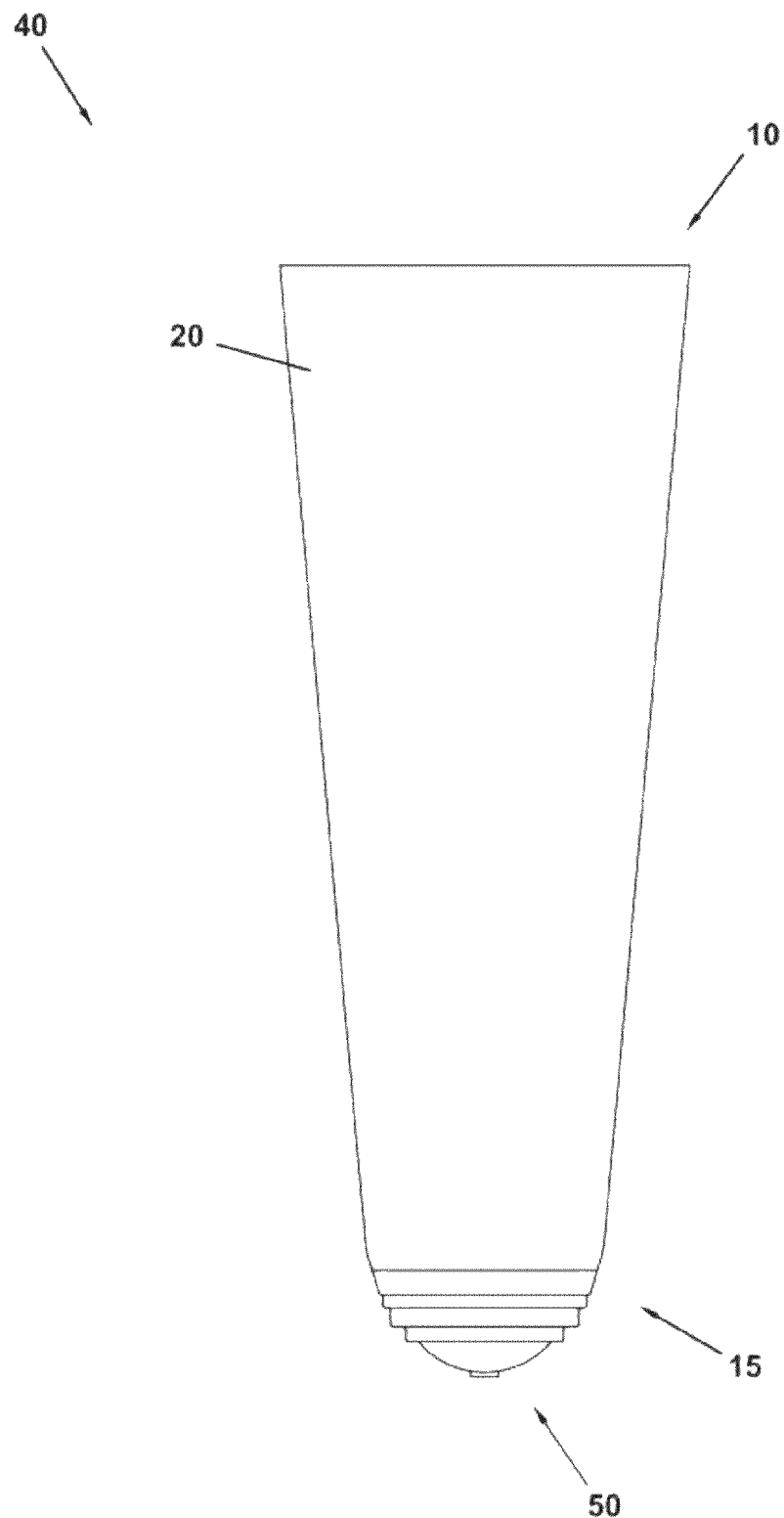
Figure 6:
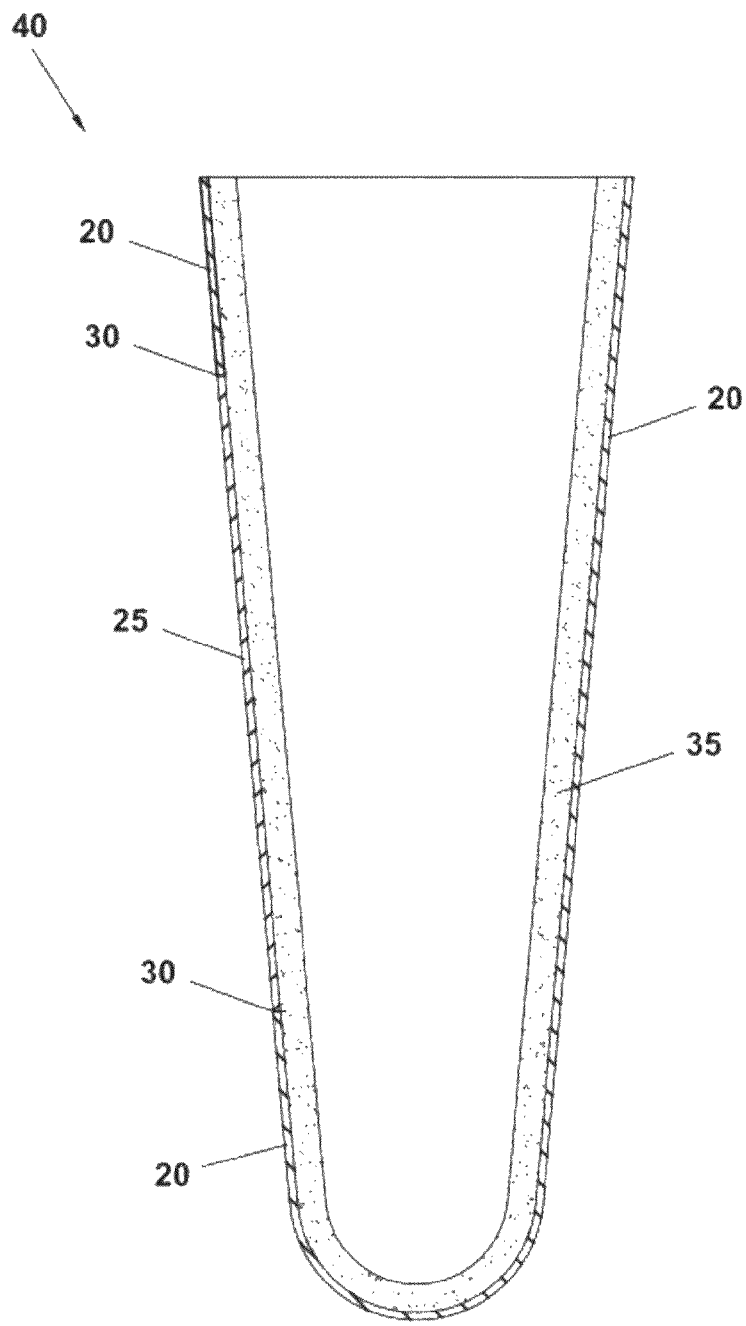
FIG. 6 is a cross-sectional view taken along line 6-6 of the liner of FIG. 5a, wherein the docking element shown therein has been removed for clarity.

An alternate embodiment of a controlled-stretch liner 40 of the present invention is illustrated in FIGS. 5*a*-5*b* and FIG. 6. This liner 40 is similar to the liner 5 shown in FIGS. 1*a*-1*b* and FIG. 2 but, as shown, the two-way stretch fabric panel 45 of this liner has a different shape. More particularly, the two-way stretch fabric panel 45 of this liner 40 is of oval or elliptical shape. Otherwise, all of the stretch-controlling fabric, knee panel fabric, and polymeric material properties and dimensions described above may be applied to this embodiment of the liner 40. This alternative controlled-stretch liner 40 may also include a docking element like the docking element 50 described above and depicted in FIGS. 7-8.

As described above and as shown in FIGS. 1-6, liners of the present invention may be locking liners. Accordingly, a liner of the present invention may include a docking element at the closed end thereof. The docking element may be employed to attach the liner to the socket portion of a prosthesis.

Figure 7:
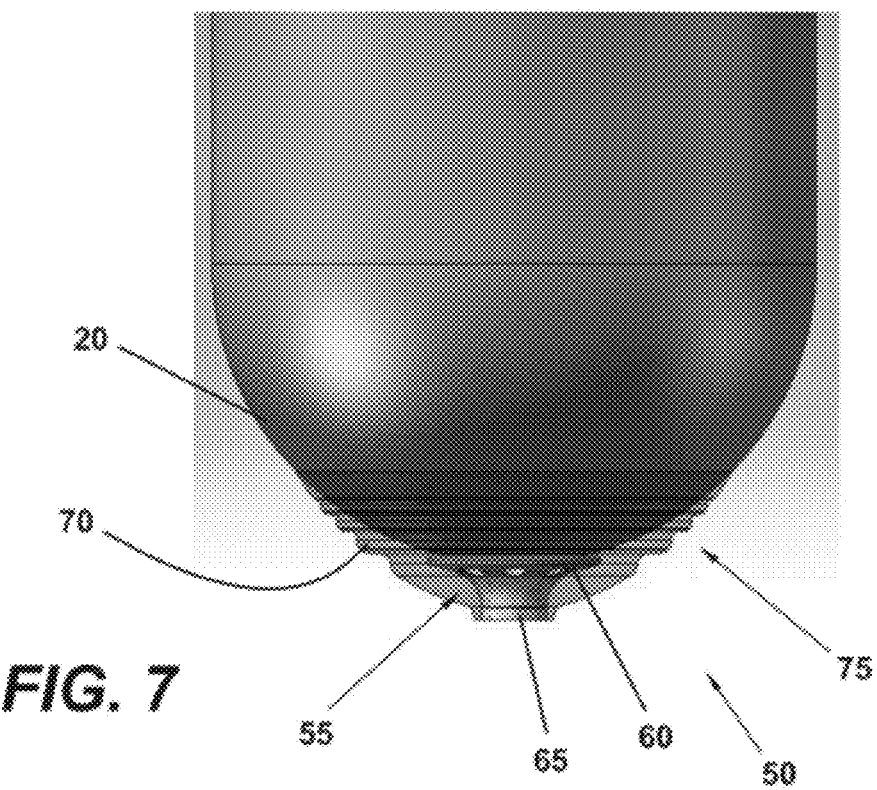
FIG. 7 is a detailed view in partial transparency of the exemplary docking element located at the closed end of the liners of FIGS. 1a-1b and 5a-5b.
Figure 8:
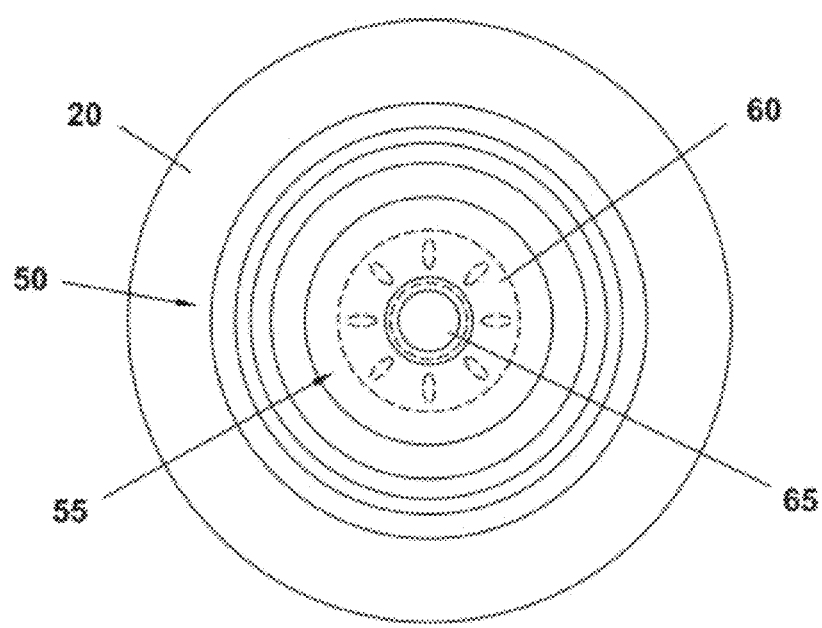
FIG. 8 is a bottom view of the docking element of FIG. 7.

As can be best observed in FIGS. 7-8, one particular embodiment of a docking element 50 of the present invention includes a metallic threaded T-nut 55 that is attached to the stretch-controlling fabric of the liner at the closed end thereof by an overlying and substantially encasing semi-flexible umbrella 70.

As shown, the T-nut 55 portion of the docking element 50 includes a base portion 60 from which extends a hollow, internally-threaded boss 65. Preferably, at least the interior surface of the base portion 60 of the T-nut 55 is concave so as to better conform to the rounded distal shape of the liner once a residual limb is inserted therein. The threaded boss 65 is provided to receive and retain a like-threaded pin, lanyard connector or other connecting element (not shown) that can be used to attach the liner to a mating docking component associated with a socket of a prosthesis. Such connecting elements are well know to those of skill in the art.

The encasing umbrella portion 70 of the docking element 50 may be comprised of polyurethane, which bonds to the fabric at the closed end of the liner and secures the T-nut 55 in position thereon. It may also be possible to substitute a hard silicone rubber or another similar material for the umbrella 70. The design of this umbrella 70 differs from know designs in that this umbrella is preferably provided with an accordion configuration. That is, as best shown in FIGS. 7-8, the umbrella 70 has a stepped configuration 75 that allows for a slight collapse or compression of the umbrella as the weight of an amputee presses the closed end of an associated liner into the bottom of the prosthetic socket. By allowing for a slight collapse or compression of the umbrella 70, the docking element 50 is able to better conform to the shape of a residual limb, thereby providing increased comfort for amputees. While described herein only with respect to a controlled-stretch liner of the present invention, it should be apparent to one of skill in the art that such a docking element, or the T-nut or umbrella thereof, could be used with other liners as well.

While certain embodiments of the present invention are described in detail above, the scope of the invention is not to be considered limited by such disclosure, and modifications are possible without departing from the spirit of the invention as evidenced by the following claims:

What is claimed is:

1. A controlled-stretch prosthetic liner for use as a standalone residual limb-prosthetic socket interface, comprising:

a fabric covering having an open end for introduction of a residual limb and a closed end opposite said open, said fabric covering further comprising:

a stretch-controlling fabric portion extending from said closed end, said stretch-controlling fabric having a limited stretch direction with a range of elasticity of between about 10-40%, a non-limited stretch direction with a range of elasticity of between about 70-250%, and a modulus in the non-limited stretch direction of between about 0.5-12.0 lbf., said stretch-controlling fabric oriented such that said limited stretch direction is directed along the length of said liner, and a two-way stretch fabric portion joined to said stretch-controlling fabric portion, said two-way stretch fabric portion located to overlie a joint of a residual limb when said liner is worn, said two-way stretch fabric portion comprised of a fabric having a range of elasticity of between about 70-250% in both directions and a 50% modulus of between about 0.9-11.25 lbf.;

a continuous layer of a cushioning and shape-conforming polymeric material residing on only an interior surface of said fabric covering, said polymeric material extending from said closed end of said fabric covering at least a distance that is substantially equivalent to the depth of a prosthetic socket with which said covering will be used; and a docking element located at the closed end of said fabric covering for attaching the liner to a socket portion of a prosthetic limb;

whereby, when said liner is used by an amputee with a prosthetic limb, said stretch-controlling fabric portion of said fabric covering will act to limit longitudinal stretching of said liner while said two-way stretch fabric portion of said fabric covering will concurrently permit adequate flexion of a joint of the amputee's residual limb.

2. The liner of claim 1, wherein said stretch-controlling fabric has a range of elasticity of less than 30% in said limited stretch direction.

3. The liner of claim 1, wherein said stretch-controlling fabric has a range of elasticity of between about 140-190% in said non-limited stretch direction.

4. The liner of claim 1, wherein said stretch-controlling fabric has a modulus of between about 0.5-2.0 lbf. in said non-limited stretch direction.

5. The liner of claim 1, wherein said stretch-controlling fabric has a weight of between about 12-22 oz./sq. yd.

6. The liner of claim 1, wherein said stretch-controlling fabric is of rib knit construction and includes nylon 6,6.

7. The liner of claim 6, further comprising elastic cord inserted into at least some of the courses of said rib knit fabric.

8. The liner of claim 1, wherein said two-way stretch fabric has a range of elasticity of between about 100-130% in both directions.

9. The liner of claim 1, wherein said two-way stretch fabric has a 50% modulus of at least about 3.25 lbf.

10. The liner of claim 1, wherein said two-way stretch fabric forms a panel of between about 1.8-3.8 inches in width as measured radially between linear tangent points of said panel and said stretch-controlling fabric.

11. The liner of claim 1, wherein said two-way stretch fabric forms a panel having a width of between about 40-100% of the full lay-flat width of the associated liner as measured between linear tangent points of said panel and said stretch-controlling fabric.

12. The liner of claim 1, wherein said polymeric material is a block copolymer and mineral oil gel composition.

13. The liner of claim 12, wherein said block copolymer and mineral oil gel composition is reinforced with KEVLAR.

14. The liner of claim 1, wherein said polymeric material tapers from a greater thickness at said closed end of said fabric covering to a lesser thickness at said open end of said fabric covering.

15. The liner of claim 14, wherein said polymeric material tapers substantially symmetrically from said closed end to said open end of said fabric covering.

16. The liner of claim 14, wherein said polymeric material tapers substantially asymmetrically along anterior and posterior sections of said fabric covering, with said polymeric material located along said anterior portion being thicker than said polymeric material located along said posterior portion at any given distance from said closed end.

17. The liner of claim 1, wherein said docking element includes a metallic base with an internally threaded boss extending therefrom.

18. The liner of claim 17, wherein said docking element is bonded to said fabric covering by an overlying umbrella of polyurethane.

19. The liner of claim 1, wherein a controlled-stretch portion of said liner exhibits an elasticity in a longitudinal direction of between about 15-25%, an elasticity in a circumferential direction of between about 90-130%, and has a 50% modulus in the circumferential direction of between about 1.0-2.0 lbf.

20. A controlled-stretch prosthetic liner for use as a standalone residual limb-prosthetic socket interface, comprising:
a fabric covering having an open end for introduction of a residual limb and a closed end opposite said open, said fabric covering designed to control the elasticity of said liner in a longitudinal and circumferential direction, said fabric covering further comprising:
a stretch-controlling fabric portion extending from said closed end, said stretch-controlling fabric having a limited stretch direction with a range of elasticity of less than about 30%, a non-limited stretch direction with a range of elasticity of between about 140-190%, a modulus in the non-limited stretch direction of between about 0.5-2.0 lbf., and a weight of between about 12-22 oz./sq. yd, said stretch-controlling fabric oriented such that said limited stretch direction extends in the longitudinal direction of said liner, and
a two-way stretch fabric portion located within an opening in said stretch-controlling fabric portion, said two-way stretch fabric portion forming a panel of between about 1.8-3.8 inches in radial width, said panel joined to said stretch-controlling fabric portion and located to overlie a joint of a residual limb when said liner is worn, said two-way stretch fabric portion comprised of a fabric having a range of elasticity of between about 100-130% in both directions and a 50% modulus of at least about 3.25 lbf.;
a continuous layer of a cushioning and shape-conforming block copolymer and mineral oil gel composition residing on only an interior surface of said fabric covering, said block copolymer and mineral oil gel composition extending from said closed end of said fabric covering at least a distance that is substantially equivalent to the depth of a prosthetic socket with which said covering will be used; and
a docking element located at the closed end of said fabric covering for attaching said liner to a socket portion of a prosthetic limb;
whereby, when said liner is used by an amputee with a prosthetic limb, said stretch-controlling fabric portion of said fabric covering will act to limit longitudinal stretching of said liner while said two-way stretch fabric portion of said fabric covering will concurrently permit adequate flexion of a joint of the amputee's residual limb.

21. The liner of claim 20, wherein said stretch-controlling fabric is of a rib knit construction that includes elastic cord inserted into at least some of the courses thereof.

22. The liner of claim 20, wherein said block copolymer and mineral oil gel composition includes KEVLAR that reinforces said gel composition and assists with liner stretch control.

23. The liner of claim 20, wherein a controlled-stretch portion thereof exhibits an elasticity in a longitudinal direction of between about 15-25%, an elasticity in a circumferential direction of between about 90-130%, and has a 50% modulus in the circumferential direction of between about 1.0-2.0 lbf., and wherein said liner in the area of said panel of two-way stretch fabric exhibits an elasticity of 60% or greater in both the longitudinal and circumferential directions, and has a 50% modulus of between about 1.0-3.0 lbf.

24. A controlled-stretch below-knee prosthetic liner for use as a standalone residual leg-prosthetic socket interface, comprising:
a fabric covering having an open end for introduction of a residual leg and a closed end opposite said open, said fabric covering designed to control the elasticity of said liner in a longitudinal and circumferential direction, said fabric covering further comprising:
a stretch-controlling fabric portion extending from said closed end, said stretch-controlling fabric having a limited stretch direction with a range of elasticity of less than about 30%, a non-limited stretch direction with a range of elasticity of between about 140-190%, a modulus in the non-limited stretch direction of between about 0.5-2.0 lbf., and a weight of between about 12-22 oz./sq. yd, said stretch-controlling fabric oriented such that said limited stretch direction extends in the longitudinal direction of said liner,
a two-way stretch fabric portion located within an opening in said stretch-controlling fabric portion, said two-way stretch fabric portion forming a panel of between about 1.8-3.8 inches in width and joined to said stretch-controlling fabric portion by a sewn seam, said panel located to overlie the knee joint of a residual leg when said liner is worn and comprised of a fabric having a range of elasticity of between about 100-130% in both directions and a 50% modulus of less than about 3.25 lbf.;
a continuous layer of a cushioning and shape-conforming block copolymer and mineral oil gel composition residing on only an interior surface of said fabric covering, said block copolymer and mineral oil gel composition extending from said closed end of said fabric covering at least a distance that is substantially equivalent to the depth of a prosthetic socket with which said covering will be used; and
a docking element located at the closed end of said fabric covering for attaching said liner to a socket portion of a prosthetic leg;
wherein a controlled-stretch portion of said liner exhibits an elasticity in a longitudinal direction of between about 15-25%, an elasticity in a circumferential direction of between about 90-130%, and has a 50% modulus in the circumferential direction of between about 1.0-2.0 lbf., and wherein said liner in the area of said panel of two-way stretch fabric exhibits an elasticity of 60% or greater in both the longitudinal and circumferential directions, and has a 50% modulus of between about 1.0-3.0 lbf.; and whereby, when said liner is used by an amputee with a prosthetic leg, said stretch-controlling fabric portion of said fabric covering will act to limit longitudinal stretching of said liner while said two-way stretch fabric portion of said fabric covering will concurrently permit adequate flexion of a knee joint of the amputee's residual leg.

25. The liner of claim 24, wherein said stretch-controlling fabric is of a rib knit construction that includes elastic cord inserted into at least some of the courses thereof.

26. The liner of claim 24, wherein said block copolymer and mineral oil gel composition includes KEVLAR that reinforces said gel composition and assists with liner stretch control.

27. A controlled-stretch prosthetic liner for use as a standalone residual limb-prosthetic socket interface, comprising:

a fabric covering having an open end for introduction of a residual limb and a closed end opposite said open, said fabric covering further comprising:

a stretch-controlling fabric portion extending from said closed end, said stretch-controlling fabric having a limited stretch direction and a non-limited stretch direction, said stretch-controlling fabric oriented such that said limited stretch direction is directed along the length of said liner, and a two-way stretch fabric portion joined to said stretch-controlling fabric portion, said two-way stretch fabric portion located to overlie a joint of a residual limb when said liner is worn;

a continuous layer of a cushioning and shape-conforming polymeric material residing on only an interior surface of said fabric covering, said polymeric material extending from said closed end of said fabric covering at least a distance that is substantially equivalent to the depth of a prosthetic socket with which said covering will be used; and a docking element located at the closed end of said fabric covering for attaching the liner to a socket portion of a prosthetic limb;

whereby, a controlled-stretch portion of said liner exhibits an elasticity in a longitudinal direction of between about 15-25%, an elasticity in a circumferential direction of between about 90-130%, and has a 50% modulus in the circumferential direction of between about 1.0-2.0 lbf.; and whereby said liner in the area of said two-way stretch fabric portion, exhibits an elasticity of 60% or greater in both the longitudinal and circumferential directions, and has a 50% modulus of between about 1.0-3.0 lbf.

* * * * *